United States Patent [19]
Yoshida

[11] Patent Number: 5,662,098
[45] Date of Patent: Sep. 2, 1997

[54] INJECTOR-TYPE ATOMIZER

[75] Inventor: Norio Yoshida, Ichikawa, Japan

[73] Assignee: Keytron Co., Ltd., Tokyo, Japan

[21] Appl. No.: 596,112

[22] PCT Filed: May 29, 1995

[86] PCT No.: PCT/JP95/01026

§ 371 Date: Jan. 30, 1996

§ 102(e) Date: Jan. 30, 1996

[87] PCT Pub. No.: WO95/32750

PCT Pub. Date: Dec. 7, 1995

[30] Foreign Application Priority Data

May 31, 1994 [JP] Japan ................................. 6-118036
Jul. 21, 1994 [JP] Japan ................................. 6-190187

[51] Int. Cl.⁶ .................................................. A61M 11/00
[52] U.S. Cl. ..................... 128/200.22; 128/203.22; 128/203.23; 128/203.28; 128/207.18; 222/386; 239/327; 239/328; 417/437
[58] Field of Search .................. 128/200.22, 203.22, 128/203.23, 203.28, 207.18, 205.14; 222/386; 239/327, 328; 417/437

[56] References Cited

U.S. PATENT DOCUMENTS

| | | | |
|---|---|---|---|
| 2,224,018 | 12/1940 | Holtman | 604/217 |
| 4,133,313 | 1/1979 | Sneider | 604/216 |
| 5,129,550 | 7/1992 | Eschbach | 239/327 |
| 5,501,373 | 3/1996 | Galli | 222/386 |
| 5,511,538 | 4/1996 | Haber et al. | 128/200.22 |

*Primary Examiner*—V. Millin
*Assistant Examiner*—William J. Deane, Jr.
*Attorney, Agent, or Firm*—Lowe, Price, LeBlanc & Becker

[57] ABSTRACT

An injector-type atomizer with a simple structure which is capable of stepwise spraying a medicament such as vaccine drawn into a cylinder by a regular amount. The atomizer comprises a cylinder having a spray nozzle at a front end thereof, a piston fitted into the cylinder and a rod having a front end attached to the piston and a rear end projecting from a rear end of the cylinder. Between the cylinder and the rod there is provided an elastic member which is crushable in a stepwise manner or an engagement mechanism in which the engagement is released by a predetermined pushing force.

10 Claims, 8 Drawing Sheets

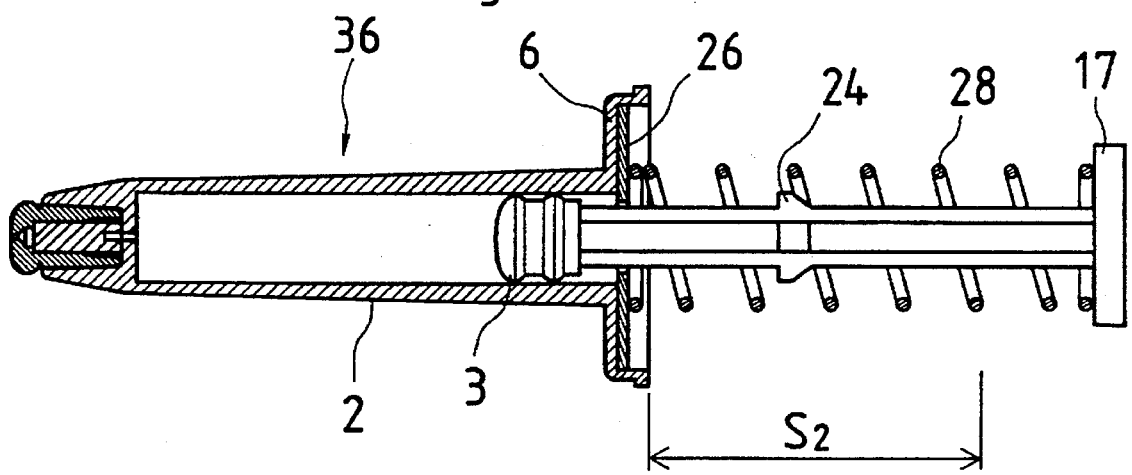
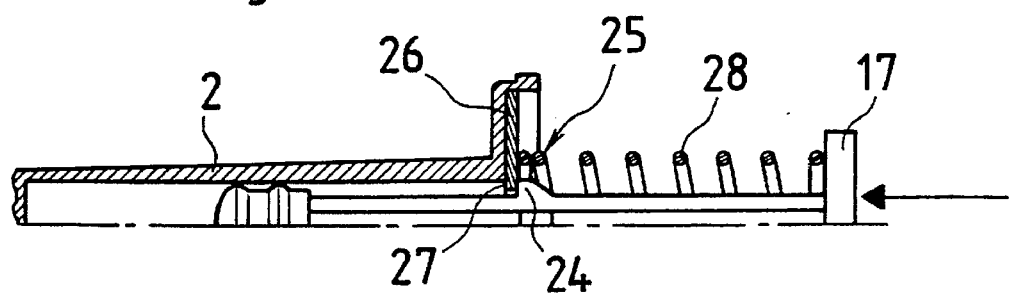
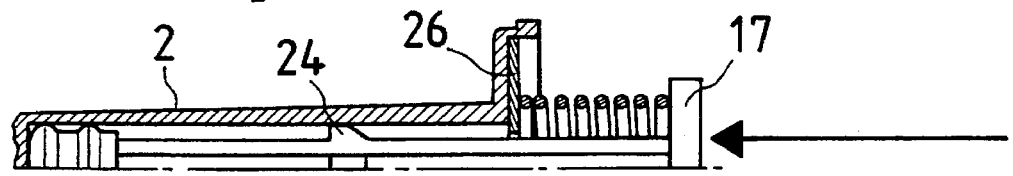

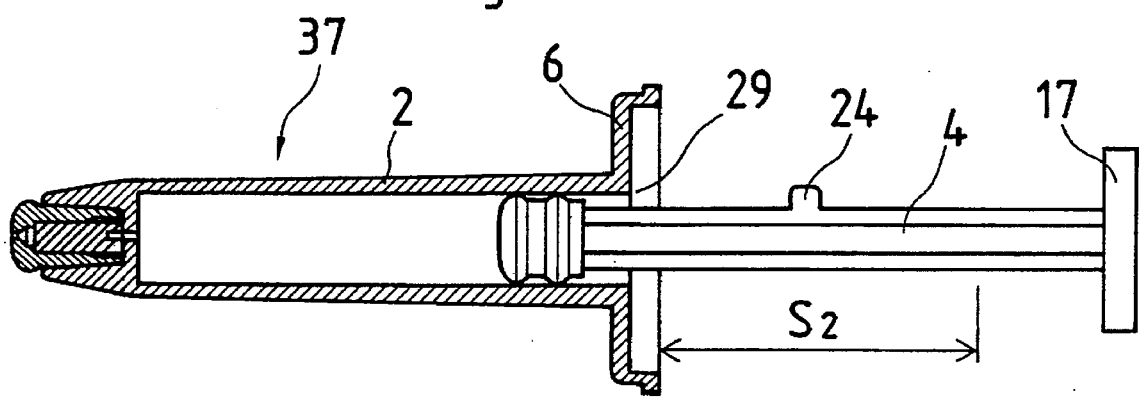
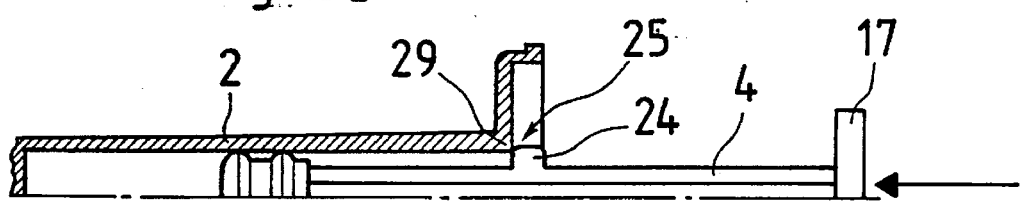
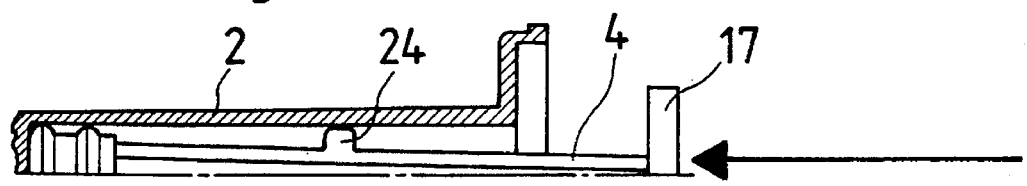

INJECTOR-TYPE ATOMIZER

TECHNICAL FIELD

The present invention relates to an injector-type atomizer for dosing a medicament such as a vaccine by spraying it to one's nasal mucous membrane.

BACKGROUND ART

An injector-type atomizer includes a cylinder and a piston and is used as a medical instrument for spraying a medicament, which has been drawn into the cylinder, from a spray nozzle at a front end of the cylinder by pressing the piston.

For a vaccine against the virus communicable through the air such as the influenza virus, it is considered most effective to be applied to the nasal mucous membrane which is infected first. Also, it has been found that the vaccine is effective even if it is sprayed to one's nasal mucous membrane instead of being injected into one's vein as has conventionally been so. Thus, the atomizer method is especially preferable for infants, since it does not cause any pain.

A conventional injector-type atomizer has a structure for merely pushing out a medicament drawn into the cylinder, and ordinarily the cylinder is filled with one dosage of the medicament. There is another type of atomizer in which several dosages of medicament are drawn into the cylinder at a time, and the medicament is sprayed dividing it into several dosages. However, a dosage of medicament sprayed (pushed out) at a time is adjusted at a rough estimate or a rule of thumb of a user, so that the user is required to get well accustomed to its use. For example, in applying a vaccine it is important to determine the dosage accurately.

Japanese Patent Laid-Open Publication No. 5-192402 discloses an injector in which a piston rod is formed with several grooves, and the distal end of a pin pushed out by a spring on the cylinder side is engaged with these grooves so that the piston rod is moved stepwise. According to the injector, a solution in the injector can be injected into an objective container surely and accurately by a regular amount by taking several actions. However, in order to make the rod to move stepwise, additional members such as springs and pins, and an additional process for providing the rod with grooves are needed to cause the increase in the manufacturing cost of the injector. Moreover, as the pin which is urged by the spring pushes the rod from one side, the rod is liable to be deformed. For this reason, the movement of rod becomes unstable, and removal and refitting of the pin fitted in the groove is troublesome in using. It is noted that the injector disclosed in the above publication is not an atomizer for spraying a medicament.

DISCLOSURE OF THE INVENTION

An object of the present invention is to provide an injector-type atomizer of a simple structure, which is capable of stepwise spraying a medicament such as vaccine drawn into a cylinder.

According to an aspect of the present invention, the injector-type atomizer comprises a cylinder having a spray nozzle attached to a front end thereof, a piston fitted into the cylinder, a rod having a front end attached to the piston and a rear end projecting from a rear end of cylinder, and an elastic member arranged to connect the rear end of cylinder and the rear end of rod, and is crushable in a stepwise manner in response to a pushing force applied in an axial direction of to the rod.

A flange is formed integrally with the rear end of the cylinder, and the elastic member may be formed into a shape of a conical dome bulging from the rear end of the rod to the peripheral edge of the flange. At an inner intermediate portion of the interior of the elastic member, an annular support portion may be formed for abutting against the flange when the elastic member is crushed.

Also, the elastic member may be composed of two of large and small rings interposed between the rear end of rod and the flange.

A length of the elastic member in the axial direction of the rod, which is reduced when the elastic member is crushed, may be set to ½ of an effective pushing stroke of the rod. The elastic member may be made of elastomer.

According to another aspect of the present invention, an injector-type atomizer comprises a cylinder having a spray nozzle attached to a front end thereof, a piston fitted into the cylinder, a rod having a front end attached to the piston and a rear end projecting from a rear end of the cylinder and an engagement mechanism for engaging the rod with the rear end of the cylinder when the rod advances by ½ of an effective pushing stroke of the rod, wherein the engagement of the rod with the rear end of the cylinder is released by a pushing force in the axial direction of the rod.

The above engagement mechanism may be composed of a protrusion radially projecting from a surface of the rod and a flexible annular ring attached to the rear end of the cylinder and having a stopper portion on the movement path of the protrusion. The engagement is released when the stopper portion annular ring is deformed by a pushing force in the axial direction of the rod.

Moreover, the above engagement mechanism may be composed of a protrusion radially projecting from the surface of the rod and an inner peripheral edge of the rear end of the cylinder. The engagement is released when the protrusion is advanced to fit into the cylinder by a pushing force in the axial direction of the rod.

The movement of the rod can be stepwise in the axial direction of the rod by the elastic member which is crushed stepwise in response to a pushing force in the axial direction of the rod, or by the engagement mechanism interposed between the cylinder and the rod.

BRIEF DESCRIPTION OF THE DRAWINGS

FIG. 12 is a vertical sectional view of an injector-type atomizer according to the sixth embodiment of the present invention;

FIG. 13a is a partially sectional view showing a state in which a rod of the atomizer shown in FIG. 12 is advanced at a first stage;

FIG. 13b is a partially sectional view showing a state in which the rod of the atomizer shown in FIG. 12 is advanced at a second stage;

FIG. 14 is a vertical sectional view of an injector-type atomizer according to the seventh embodiment of the present invention;

FIG. 15a is a partially sectional view showing a state in which a rod of the atomizer shown in FIG. 14 is advanced at a first stage; and FIG. 15b is a partially sectional view showing a state in which the rod of the atomizer shown in FIG. 14 is advanced at a second stage.

BEST MODE OF CARRYING OUT THE INVENTION

Figure 1:
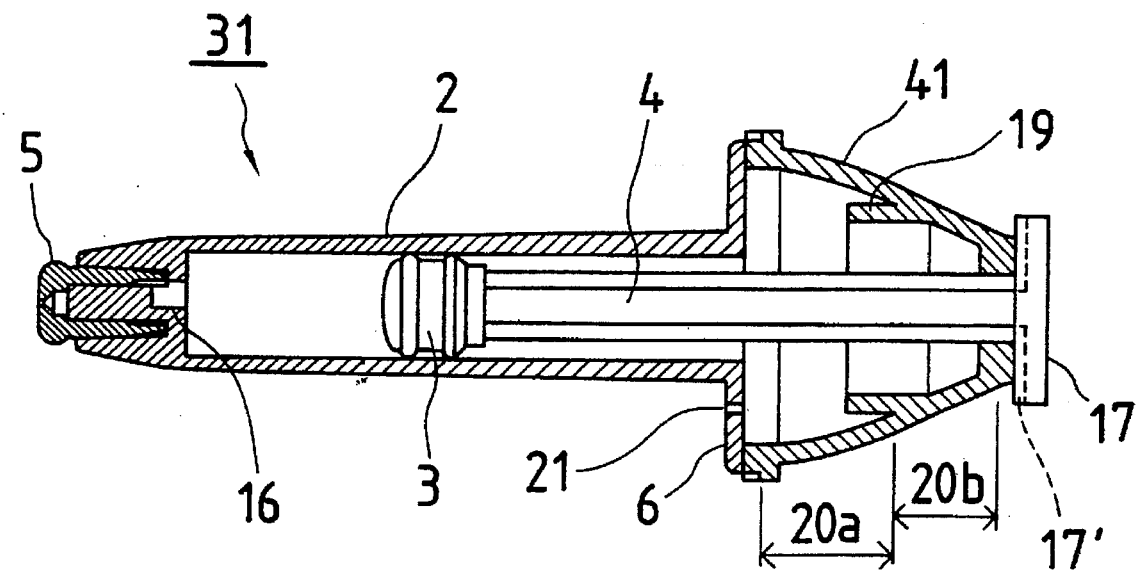
FIG. 1 is a vertical sectional view showing the whole structure of an injector-type atomizer according to the first embodiment of the present invention.
Figure 3:
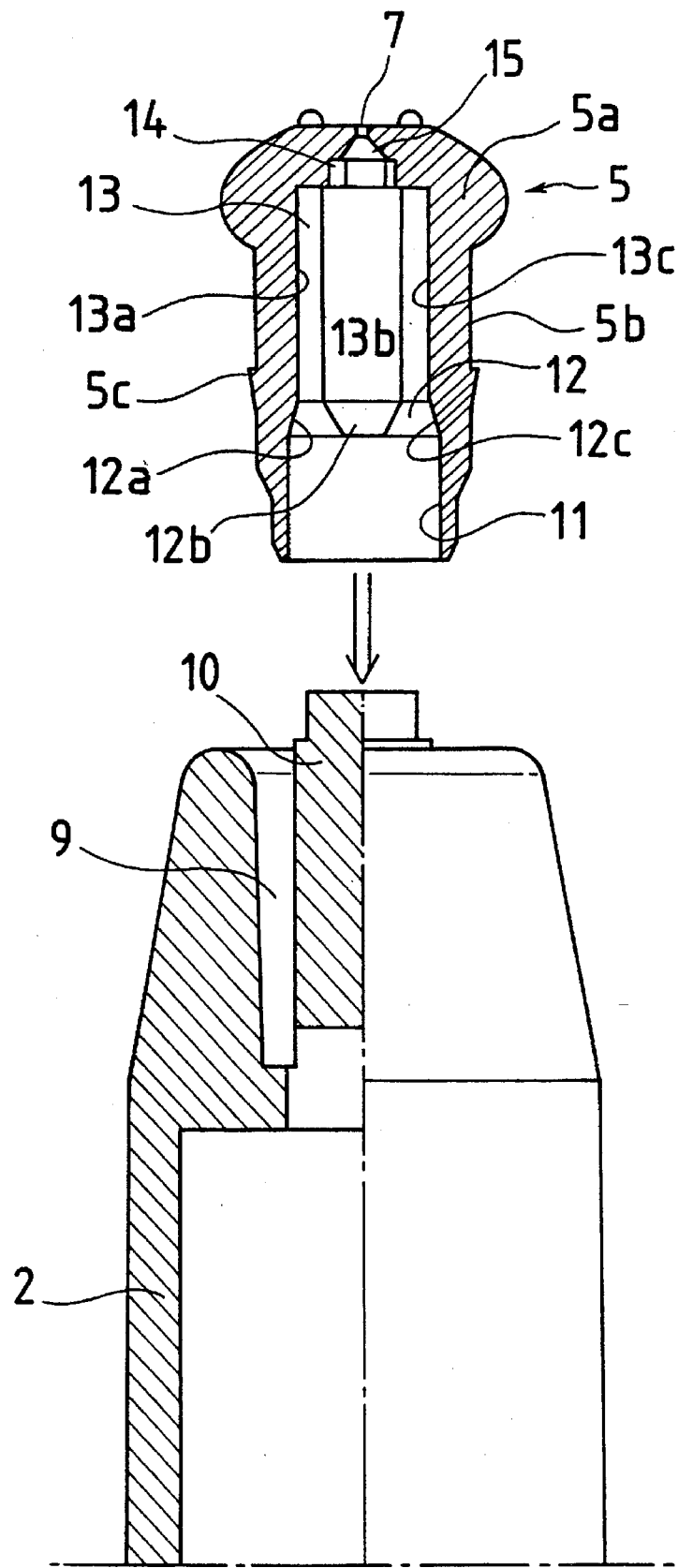
FIG. 3 is a vertical sectional view of a spray nozzle and a front end of a cylinder.

As shown in FIG. 1, an injector-type atomizer 31 according to the first embodiment includes a cylinder 2, a piston 3 and a rod 4. The cylinder 2 is made of polypropylene or polyethylene, and is formed with a wide flange 6 at a rear end thereof. A spray nozzle 5 molded out of the same material as the cylinder 2 is attached to a front end of the cylinder 2. As shown in FIG. 3, the spray nozzle 5 comprises a bulged portion 5a having a spray port 7 formed in a center of the distal end thereof, and a cylindrical portion 5b extending backward from the bulged portion 5a. The spray nozzle 5 is pressed to fit into an annular deep groove 9 formed on a distal end of cylinder 2. The cylinder 2 is formed with a core 10 at a center of a front end thereof and the core 10 is inserted into the spray nozzle 5.

The outer peripheral surface of the cylindrical portion 5b of spray nozzle 5 is formed with an annular ridge 5c having a wedge-shaped section in order to make the attachment easy. The inner peripheral surface 11 on a rear end of the cylindrical portion 5a has a diameter larger than an outer diameter of the core 10. An inner surface 13 near the front end is formed with four flat wall faces 13a, 13b, 13c and 13d. A distance between each opposite wall faces is set to be substantially equal to the outer diameter of the core 10. A middle inner peripheral surface 12 is constituted of inclined planes 12a, 12b, 12c and 12d continuing respectively to wall surface 13a–13d of the inner peripheral surface 13 near the front end of the spray nozzle 5 and also to the inner peripheral surface 11 near a rear end of the spray nozzle 5, whereby the core 10 can easily be inserted into the inner peripheral surface 13. When the spray nozzle 5 is attached to the cylinder 2, the core 10 abuts internally against the four wall faces 13a–13d of the inner peripheral surface 13, and a clearance defined between the outer peripheral surface of the core 10 and the inner peripheral surface 13 forms a path for the flow of liquid medicament.

Figure 4:
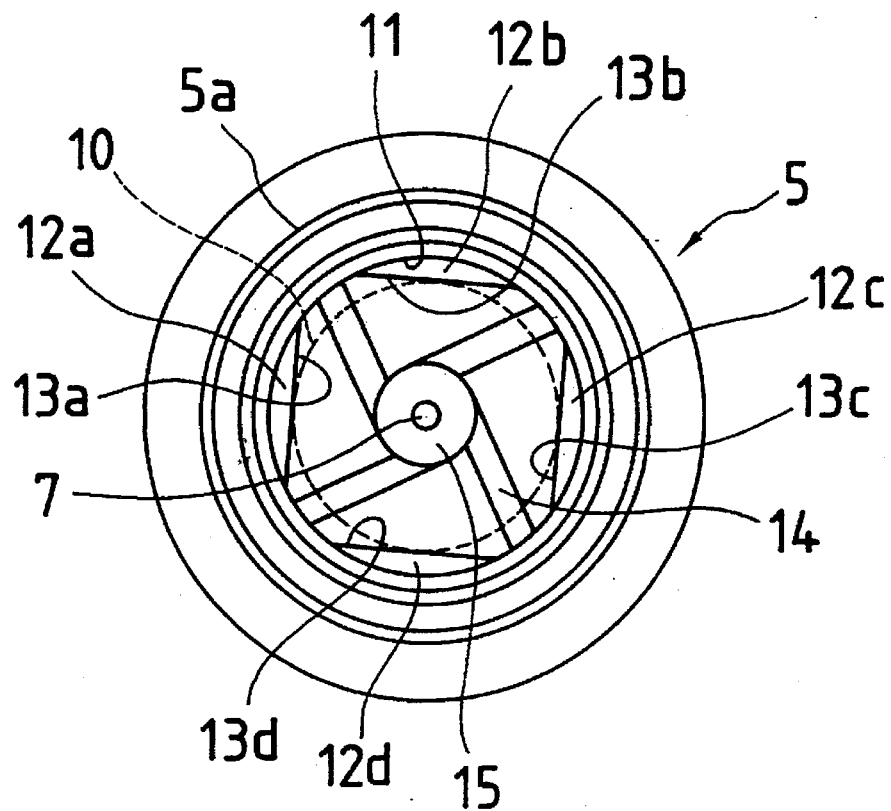
FIG. 4 is a plan view of the spray nozzle viewed from the rear.

As shown in FIG. 4, at an inner surface of the front end of the spray nozzle 5, there is formed guide grooves 14 which radially extend around the spray port 7, and a conical convergence hole 15. As shown in FIG. 3, at the front end portion of the cylinder 2, there is provided an opening 16 communicating with an inner space of the cylinder 2 and a clearance formed between the inner surface 11 near the rear end of the spray nozzle 5 and the core 10.

The liquid medicament drawn in the cylinder is guided into the annular deep groove 9 from the opening 16, and supplied to the convergence hole 15 from the guide groove through a clearance defined between the outer peripheral surface of the core 10 and the distal end inner peripheral surface 13. Then, the liquid medicament is sprayed forward from the convergence hole 15.

As shown in FIG. 1, the piston 3 is made of elastomer such as silicone rubber with a double ring-shaped protrusion on an outer periphery thereof and is fixed to a front end of the rod 4. The rod 4 made of hard polypropylene or polyethylene has the front end securely fixed to the piston 3, and a rear end projecting from the rear end of the cylinder 2 and formed with a small disc 17 for being pushed by a finger. The rod 4 has a cross-shaped section and the disc 17 is formed with channels 17' radially extending on the side near the rod. The channels communicate with recesses in the cross-shaped section. The axis of the rod coincides with that of the cylinder 2.

An elastic member 41 is mounted between the flange 6 formed on the rear end of the cylinder 2 and the disc 17 formed on the rear end of the rod 4, the elastic member 41 having a conical dome bulging from the disc 17 toward a peripheral edge of the flange. The elastic member 41 is made of a little thick elastomer (silicone rubber in the present embodiment), and is formed with an annular support portion 19 at the middle of its interior so that the distal end of the support portion abuts against the flange 6 when the elastic member 41 is crushed toward the cylinder 2.

Figure 2A:
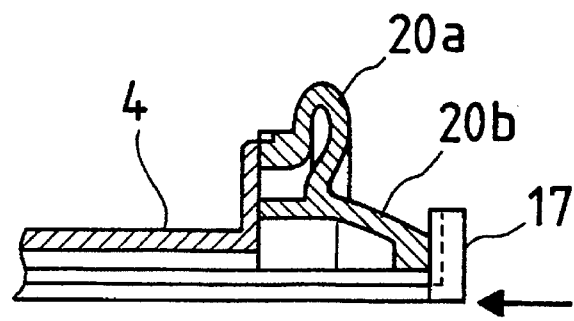
FIG. 2a is a partially sectional view showing a state in which an elastic member of the atomizer shown in FIG. 1 is crushed at a first stage.
Figure 2B:
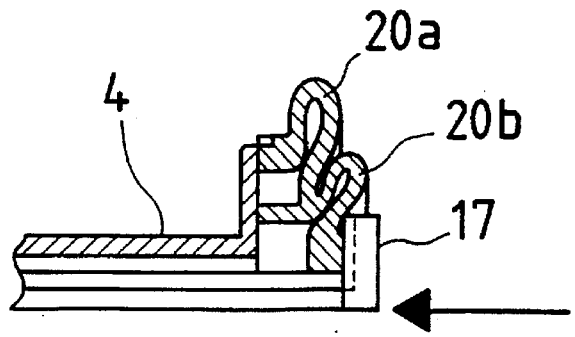
FIG. 2b is a partially sectional view showing a state in which the elastic member is crushed at a second stage.

When the rod 4 is pressed in the axial direction thereof, a first dome wall 20a between the flange 6 and the annular support portion 19 starts to be deformed, and when a pushing force reaches its predetermined first pushing force level, the annular support portion 19 abuts against the flange 6 (a first-stage shown in FIG. 2a). This state is maintained even if the pushing force acting on the rod 4 is discontinued. When the pushing force further increases and reaches a predetermined second pushing force level, a second dome wall 20b between the annular support portion 19 and the disc 17 is deformed and crushed (a second-stage shown in FIG. 2b). Thus, the rear end of the cylinder 2 is connected with the rear end of the rod 4 by the elastic member which crushes stepwise (two stages in the present embodiment) in response to the pushing force of the rod 4 in the axial direction.

In assembling an injector-type atomizer 31, the rod 4 is inserted into the elastic member 41 from the rear end thereof in a sterilized room, the piston 3 is attached to the front end of the rod 4, the piston 3 and the rod 4 are fitted into the cylinder 2, the front end of the elastic member 41 is brought to abut the flange 6 of the cylinder 2, and the rear end of the elastic member 41 is brought to abut the disc 17 on the rear end of the rod. After the medicament is drawn into the elastic member, the spray nozzle 5 is attached to the front end of the cylinder The elastic member 41 and the flange 6 are fixed to each other by a fitting structure or adhesives. Although the rear end of the elastic member 41 abuts against the rod 4, clearances are formed between the recesses in the cross-shaped section of the rod 4 elastic member 41.

In the present embodiment, the channel 17' communicating with the recesses of the rod 4 and a vent 21 formed in the flange 6 are provided for ventilation to communicate an inner space of the conical dome of the elastic member 41 with the exterior so that the dome may deform with ease.

As shown in FIG. 2, the front end of the cylinder 2 is inserted into a solution of medicament or vaccine with the rod 4 pressed to the second stage, and the medicament is drawn into the atomizer 31. After that the spray nozzle 5 is attached to the front end of the cylinder 2.

In use of the injector-type atomizer 31, the spray nozzle 5 is inserted into a naris of a subject of medication, and the rod 4 is pressed to the first stage by pushing the disc 17 with a finger. In this manner, a predetermined dosage of medicament or vaccine can be accurately given to the subject of medication through the nasal mucous membrane. The user can clearly sense that the rod 4 has reached an end of the first stage as the resisting force is produced when the distal end of the annular support portion 19 comes to abut the flange 6. This state is maintained even if the finger of the user moves apart from the disc 17. Subsequently, the injector-type atomizer is inserted into the other naris keeping the state, and the rod 4 is pressed to the second stage, thereby a predetermined dosage of medicament or vaccine is accurately given to the subject of medication through the other naris.

The injector-type atomizer of this embodiment is discarded after the above two-stage spraying is completed and one dosage of liquid medicament drawn into the cylinder 2 is used up.

Figure 5:
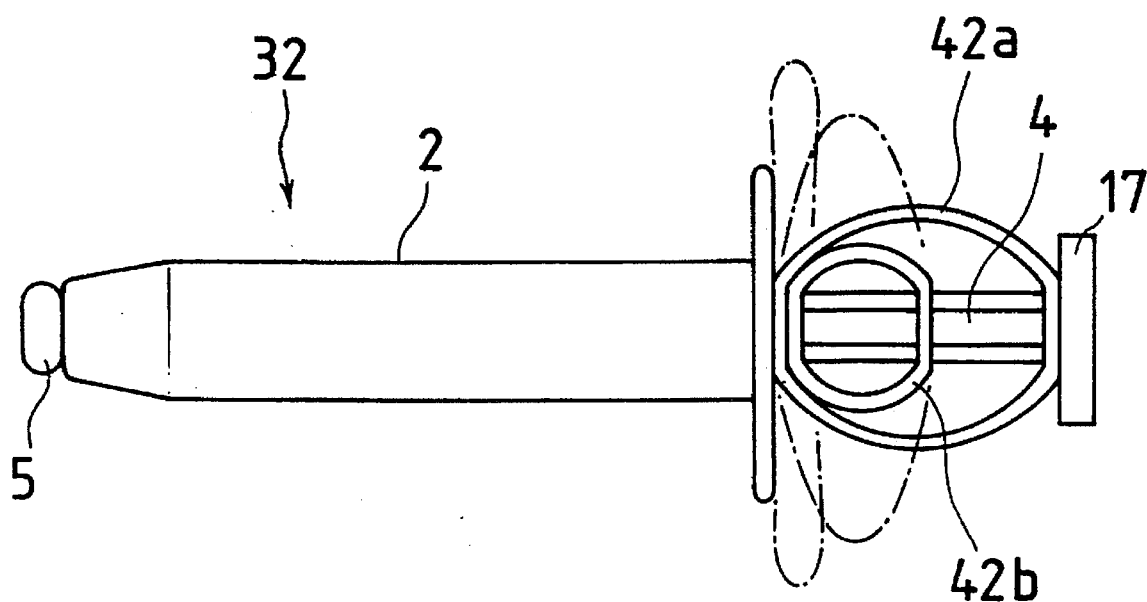
FIG. 5 is a front view showing the whole structure of an injector-type atomizer according to the second embodiment of the present invention.

FIG. 5 shows an injector-type atomizer 32 according to the second embodiment of the present invention, in which an elastic member comprises two elastic rings of a large elastic ring 42a and a small elastic ring 42b. The structure other than the elastic member is the same as that of the first embodiment. The elastic rings 42a and 42b are made of semi-hard synthetic resin (polypropylene in this embodiment). The elastic rings 42a and 42b are fitted with the rod 4 inserted into confronting portions on their diameters. When the disc 17 is pushed, the rod 4 moves to crush the large elastic ring 42a performing the first-stage spraying. The first-stage spraying is completed when the disc 17 reaches the small elastic ring 42b. The user can clearly sense the completion of the first-stage spraying as the resistance in pushing the rod 4 increases by the inner small elastic ring 42b. Further push of the rod 4 will crush both the large and small elastic rings 42a and 42b to perform the second-stage spraying.

According to this embodiment, the elastic member comprises simple rings 42a and 42b, so that the elastic member can be manufactured at lower cost.

Figure 6:
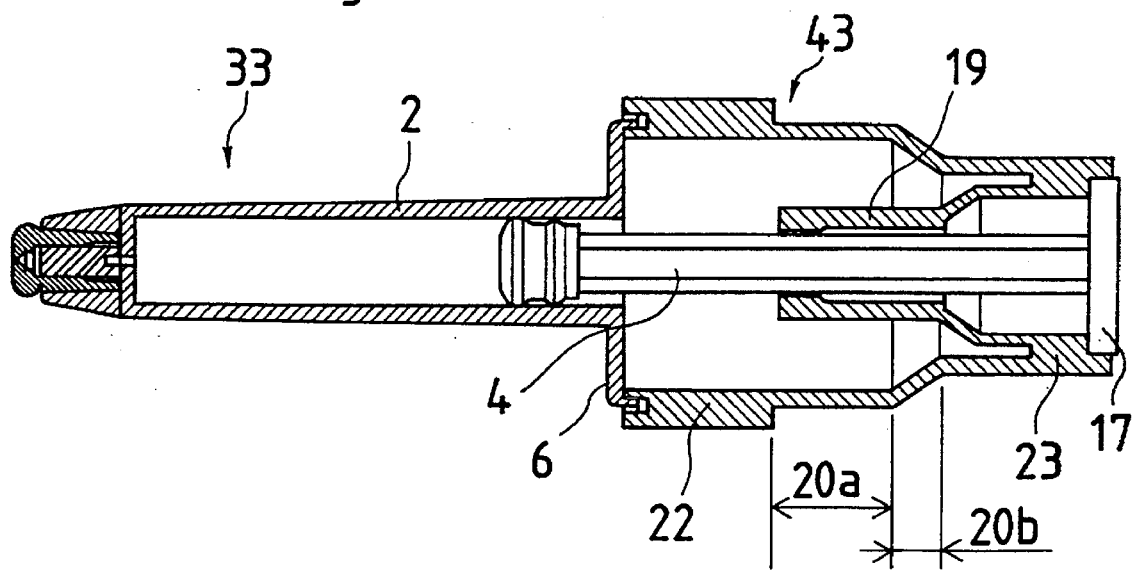
FIG. 6 is a vertical sectional view of an injector-type atomizer according to the third embodiment of the present invention.
Figure 7A:
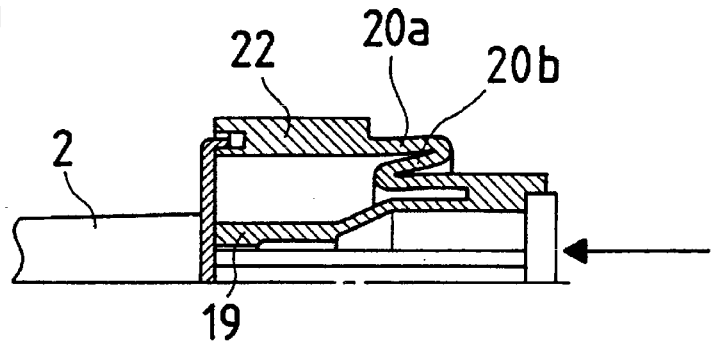
FIG. 7a is a partially sectional view showing a state in which an elastic member of the atomizer shown in FIG. 6 is crushed at a first stage.
Figure 7B:
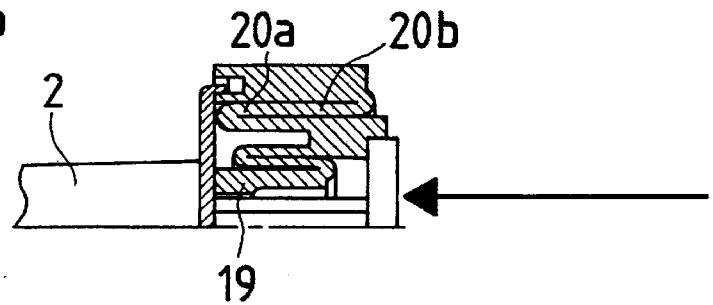
FIG. 7b is a partially sectional view showing a state in which the elastic member of the atomizer shown in FIG. 6 is crushed at a second stage.

FIG. 6 and FIGS. 7a–7b show an injector-type atomizer 33 according to the third embodiment, which characterized in shape of the elastic member and the other structure is the same as the first embodiment.

The elastic member 43 has an intermediate portion formed into a dome shape and, as a whole, presents a shape such that two cylinders of different diameters are coupled. The elastic member 43 is fitted between the flange 6 of the rear end of cylinder 2 and the disc 17 on the rear end of the rod 4. The elastic member 43 comprises a rigid cylindrical portion 22 which is formed relatively thick, a first flexible dome wall 20a which is formed relatively thin, a second dome wall 20b which is conically formed to slant, a cylindrical rear-end portion 23 and an annular support portion 19, in the order near the flange 6. The annular support portion 19 is formed to extend from the cylindrical rear-end portion 23 toward the middle of the interior of the elastic member so that the distal end of the support portion 19 abuts against a surface of the flange 6 when the support portion 19 moves forward to the cylinder 2. The elastic member 43 is made of silicone rubber.

The second dome wall 20b of the elastic member 43 is crushed by a predetermined first pushing force and the support portion 19 abuts against the flange 6 when the rod 4 is pushed in the axial direction (first stage shown in FIG. 7a). When the pushing force further increases to reach a predetermined second pushing force, the outer first dome wall 20a is crushed (second stage shown in FIG. 7b). Thus, the rear end of the cylinder 2 and the rear end of the rod 4 are connected by means of the elastic member 43 which is designed to crush stepwise in response to the pushing force of the rod 4 in the axial direction.

A structure for ventilating the interior of the elastic member 43 when being crushed is similar to that in the first embodiment.

Figure 8:
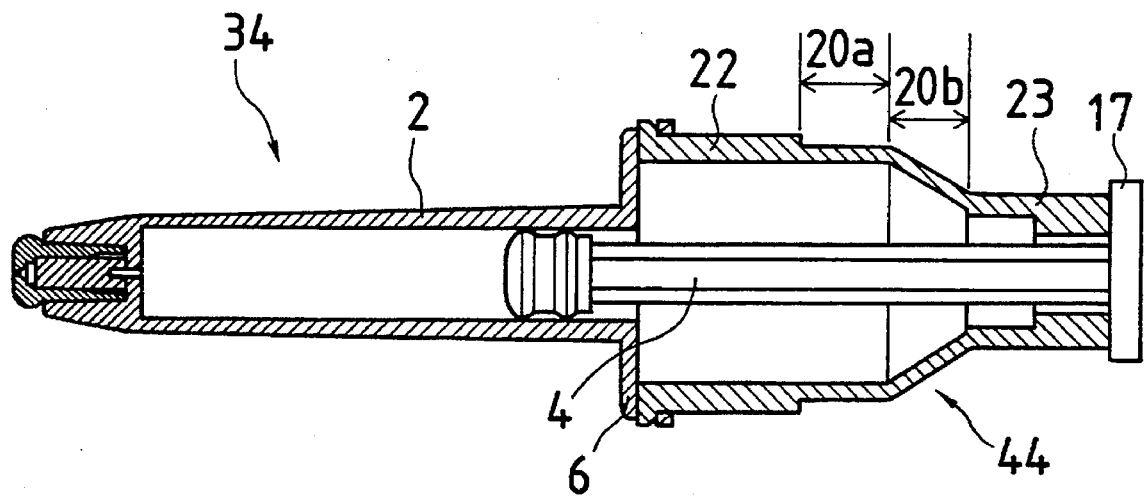
FIG. 8 is a vertical sectional view of an injector-type atomizer according to the fourth embodiment of the present invention.
Figure 9A:
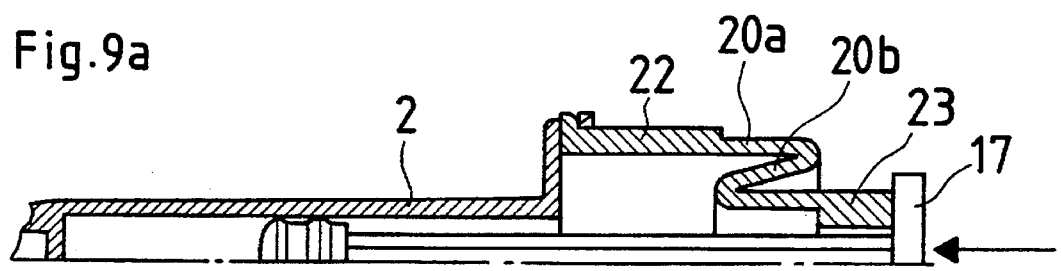
FIG. 9a is a partially sectional view showing a state in which an elastic member of the atomizer shown in FIG. 8 is crushed at a first stage.
Figure 9B:
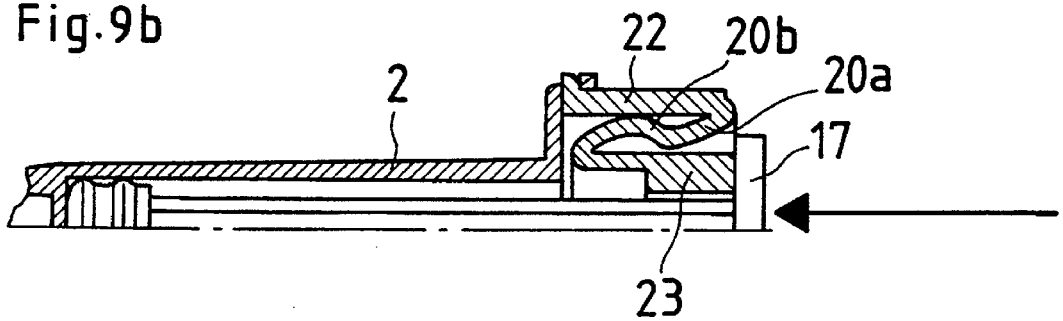
FIG. 9b is a partially sectional view showing a state in which the elastic member of the atomizer shown in FIG. 8 is crushed at a second stage.

FIG. 8 and FIGS. 9a–9b show an injector-type atomizer 34 according to the fourth embodiment, which is similar to that of the third embodiment but characterized in that the elastic member is not provided with the annular support portion. The rest of the structure is substantially the same as the third embodiment.

An elastic member 44 is made of silicone rubber, and comprises a rigid cylindrical portion 22 which is formed relatively thick, a first flexible dome wall 20a which is formed relatively thin, a second dome wall 20b which is conically formed to slant, and a cylindrical rear-end portion 23, in the order near the flange 6. When the rod 4 is pushed in the axial direction, the second dome wall 20b is first crushed by a predetermined first pushing force (first stage shown in FIG. 9a), and when the pushing force further increases to reach a predetermined second pushing force, the outer first dome wall 20a is crushed (second stage shown in FIG. 9b). Thus, the rear end of the cylinder 2 and the rear end of the rod 4 are connected by means of the elastic member 44 which is designed to crush stepwise in response to the pushing force of the rod 4 in the axial direction.

Compared with the first and the third embodiment, as the internal annular support 19 is not required in this embodiment, the structure of the mold for manufacturing the elastic member is simplified to reduce the cost of manufacturing the elastic member.

Figure 10:
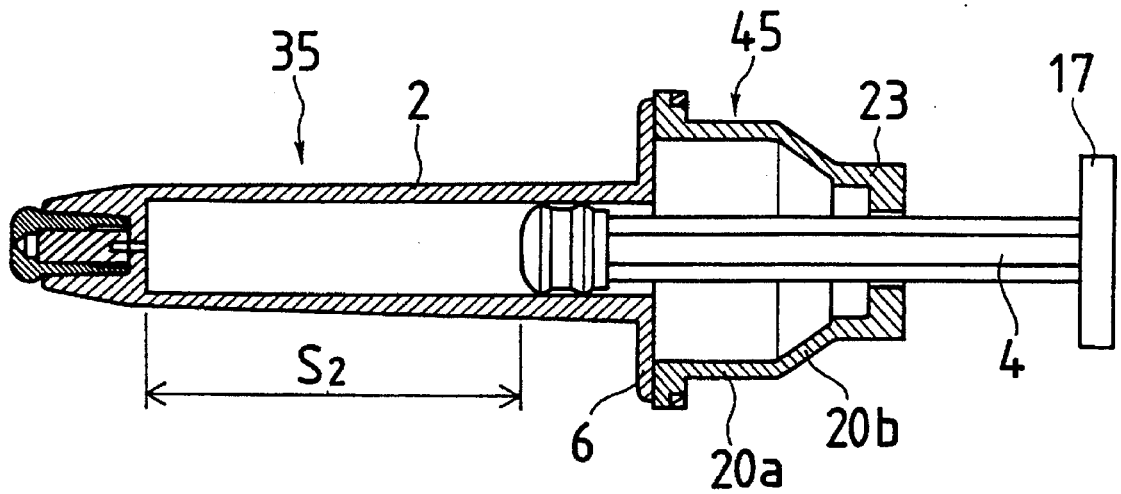
FIG. 10 is a vertical sectional view of an injector-type atomizer according to the fifth embodiment of the present invention.
Figure 11A:
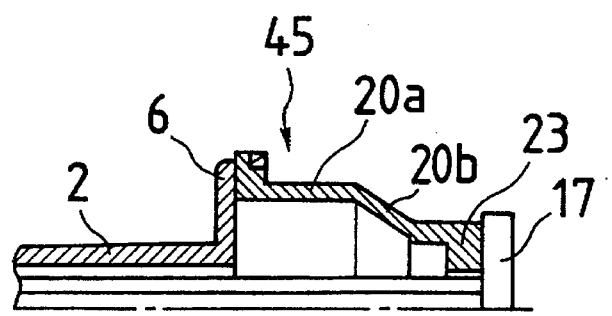
FIG. 11a is a partially sectional view showing a state in which a rod of the atomizer shown in FIG. 10 is advanced at a first stage.
Figure 11B:
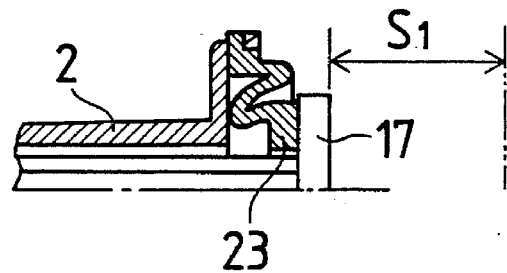
FIG. 11b is a partially sectional view showing a state in which the rod of the atomizer shown in FIG. 10 is advanced at a second stage.

FIG. 10 and FIGS. 11a–11b show an injector-type atomizer 35 according to the fifth embodiment, which is characterized by an elastic member and the rest of the structure is the same as that of the first embodiment. An elastic member 45 is made of silicone rubber and comprises a first flexible dome wall 20a of cylindrical shape which is formed relatively thin, a second dome wall 20b which is conically formed to slant, and a cylindrical rear-end cylindrical 23, in the order near the flange 6. The elastic member 45 is fitted between the rear end of the cylinder 2 and the rear end of the rod 4. The elastic member 45 is designed so that a distance S1 (FIG. 11b) of the movement of the rear end of elastic member 45 in the axial direction of the rod 4 equals ½ of an effective pushing stroke S2 (FIG. 10) of the piston 3 when the elastic member 45 is crushed. Therefore, when the elastic member 45 is left unpushed, the length of the elastic member 45 in the axial direction of the rod 4 is approximately ½ of the length of the elastic member 41 of the first embodiment. When the rod 4 is pulled backward by a distance corresponding to the effective pushing stroke S2, the rear half portion of the rod 4 projects from the elastic member 45.

The effective pushing stroke is defined by the distance between the piston 3 in contact with the front end of the cylinder 2 and the piston 3 at a position where it has been pulled backward to draw an necessary amount of the medicament into the cylinder 2 and pushed forward to purge unnecessary drawn air.

When the rod 4 is pushed in the axial direction after a medicament is drawn, the piston 3 is advanced to spray the medicament, and then the disc 17 on the rear end of the rod abuts against the rear end of the elastic member 45 (see FIG. 11a). At this position, approximately ½ of the drawn medicament is sprayed, and the user can recognize that the remainder of the medicament is ½ as a resistance is caused when pushing the rod 4. When the rod 4 is further pushed, the second dome wall 20b is crushed and subsequently the first dome wall 20a is crushed (see FIG. 11b), thereby the remaining ½ of the medicament is sprayed. Thus, the elastic member 45 is designed for spraying an amount corresponding to a liquid medicament sprayed in the second stage in the first embodiment.

When using the atomizer according to this embodiment, it is important to accurately draw an amount of medicament determined by the effective stroke.

FIG. 12 and FIGS. 13a–13b show an injector-type atomizer 36 according to the sixth embodiment. The atomizer 36 comprises a cylinder 2 with a spray nozzle 5 at a front end thereof, a piston fitted into the cylinder 2 and a rod 4 having a front end to which the piston 3 is attached and a rear end projecting from the rear end of the cylinder 2, constituting a structure similar to that of the first embodiment but differs in that an engagement mechanism 25 is provided between the rod 4 and the cylinder 2 in place of an elastic member. The engagement mechanism 25 comprises a protrusion 24 formed on the surface of the rod 4 and an annular flexible ring 26 mounted on the rear end of the cylinder 2. The protrusion 24 is situated at a distance corresponding to ½ of the effective pushing stroke S2 of the piston from the rear end of the annular ring 26. The flexible annular ring 26 has an stopper portion 27 on the moving path of the protrusion 24 together with the movement of the rod 4. The protrusion 24 can pass the stopper portion 27 of the annular ring 26 as the stopper portion 27 is deformed by the pushing force of the rod 4 in the axial direction. Further, a coil spring 28 is fitted between the flange 6 at the rear end of cylinder 2 and the disc 17 at the rear end of the rod 4 for backwardly applying an elastic force to the rod 4 when it moves forwardly. The coil spring 28 is fixed to the flange 6 and the disc 17.

When the rod 4 in a state of FIG. 12 is pushed, a medicament in the cylinder is sprayed from the spray nozzle 5. When the rod 4 is pushed until the protrusion 24 abuts against the stopper portion 27 of the annular ring 26, ½ of the medicament is sprayed. When the protrusion 24 abuts against the stopper portion 27 of the annular ring 26, a resistance is caused in moving the rod 4, thereby the user can recognize that the remainder of medicament is ½. When the rod 4 is further pushed the protrusion 24 advanced to deform the stopper portion 27 of the annular ring 26, spraying the remainder of the medicament.

In this embodiment, the backward movement of the rod 4 is limited by the coil spring 28, so that the piston 3 is prevented from slipping out of the cylinder 2. Also, the coil spring 28 gives an appropriate resistance to the forward movement of rod 4 to prevent the rod 4 from moving forward too rapidly when the engagement of the protrusion 24 with the stopper portion 27 is released.

Moreover, according to this embodiment, the mechanism for temporarily stopping the movement of the rod 4 has a simple structure composed only of the protrusion 24 and the annular ring 26 having the stopper portion 27, contributing to the lower manufacturing cost.

FIG. 14 and FIGS. 15a–15b shows an injector-type atomizer 37 according to the seventh embodiment. This embodiment is characterized by its engagement mechanism 25, and other structure is the same as that of the sixth embodiment. In this embodiment, the engagement mechanism 25 is composed of a protrusion 24 radially projecting from the surface of the rod 4 and an inner peripheral edge 29 on a rear end of the cylinder 2. The protrusion 24 is advanced into the cylinder 2 by a pushing force of the rod 4 in its axial direction to release the engagement.

In this embodiment too, when the protrusion 24 reaches the inner peripheral edge 29 on the rear end of the cylinder 2 after starting the spray of the medicament (FIG. 15a), a resistance is caused in moving the rod 4, thereby the user can recognize that the remaining medicament is ½. Subsequently, when the rod 4 is further pushed, the rod 4 advances as the protrusion 24 deforms the inner wall face of the cylinder 2, spraying the remaining medicament (FIG. 15b).

The engagement mechanism of this embodiment has a simpler structure than that of the sixth embodiment, so that the mechanism can be manufactured at a low cost.

Described in the foregoing are only some of the embodiments of the present invention and the present invention is not limited to those specific structures illustrated in the drawings. The elastic member may be or may not be fixed to both of the flange of the cylinder and the disc of the piston. In the first and fifth embodiments, the elastic member is illustrated to be a dome shape, but this member may be of a basket shape with slits parallel to the axis of the rod.

The materials of the elastic member and other parts are not limited to polypropylene and polyethylene. For sanitary reason, however, the materials of all the parts including the spray nozzle and the cylinder have to be capable of withstanding the gamma-ray or EOG sterilizing treatment.

The number of steps of movement of the rod by the elastic member may be three or more, or one. If the number of steps of movement is made one, it is convenient for drawing or administering a fixed amount of medicament.

According to the present invention, medicament or vaccine drawn into the cylinder can be divided into proper quantities and accurately administered. Moreover, as a simple mechanism is adopted for the stepwise movement of the rod for pushing the piston, and the molded product of elastic elastomer or semi-hard synthetic resin is used, the atomizer is manufactured at a low cost.

I claim:

1. An injector-type atomizer comprising:
    a cylinder having a spray nozzle at a front end thereof;

a piston fitted into said cylinder;

a rod having a front end attached to said piston and a rear end projecting from a rear end of said cylinder; and an elastic member arranged to connect the rear end of said cylinder and the rear end of said rod, and crushable in a stepwise manner in response to a pushing force applied to said rod in an axial direction thereof by a user, so that the stepwise crushing of said bag is sensible by the user.

2. The injector-type atomizer according to claim 1, wherein said cylinder has a flange formed integrally with the rear end thereof, and said elastic member is formed into a shape of a conical dome bulging from the rear end of said rod to the peripheral edge of said flange.

3. An injector-type atomizer comprising:

a cylinder having a spray nozzle at a front end thereof;

a piston fitted into said cylinder;

a rod having a front end attached to said piston and a rear end projecting from a rear end of said cylinder; and an elastic member arranged to connect the rear end of said cylinder and the rear end of said rod, and crushable in a stepwise manner in response to a pushing force applied to said rod in an axial direction thereof by a user, so that the stepwise crushing of said bag is sensible by the user, wherein:

said cylinder has a flange formed integrally with the rear end thereof;

said elastic member is formed into a shape of a conical dome bulging from the rear end of said rod to the peripheral edge of said flange; and an annular support portion is formed for abutting against said flange when said elastic member is crushed, at an inner intermediate portion of said elastic member.

4. An injector-type atomizer comprising:

a cylinder having a spray nozzle at a front end thereof;

a piston fitted into said cylinder;

a rod having a front end attached to said piston and a rear end projecting from a rear end of said cylinder and an elastic member arranged to connect the rear end of said cylinder and the rear end of said rod, and crushable in a stepwise manner in response to a user force applied to said rod in an axial direction thereof by a user, so that the stepwise crushing of said bag is sensible by the user; wherein, said elastic member comprises a first ring interposed between the rear end of said rod and said flange, and a second ring arranged inside said first ring and having a diameter smaller than a diameter of said first ring.

5. An injector-type atomizer comprising:

a cylinder having a spray nozzle at a front end thereof;

a piston fitted into said cylinder;

a rod having a front end attached to said piston and a rear end projecting from the rear end of said cylinder; and an elastic member interposed between the rear end of said cylinder and the rear end of said rod, and crushable by a pushing force in an axial direction of said rod, wherein a length of said elastic member in the axial direction of said rod, which is reduced when crushed, is set to ½ of an effective pushing stroke of said rod.

6. The injector-type atomizer according to claim 5, wherein said cylinder has a flange formed integrally with the rear end thereof, and said elastic member is formed into a shape of a conical dome tapering from a peripheral edge of said flange toward the rear end of said rod.

7. The injector-type atomizer according to claim 1, wherein said elastic member is made of a material of elastomer.

8. An injector-type atomizer comprising:

a cylinder having a spray nozzle at a front end thereof;

a piston fitted into said cylinder;

a rod having a front end attached to said piston and a rear end projecting from a rear end of said cylinder; and an engagement mechanism for engaging said rod with the rear end of said cylinder when said rod advances by ½ of an effective pushing stroke of said rod, wherein the engagement of said rod with the rear end of said cylinder is released by a pushing force in an axial direction of said rod.

9. The injector-type atomizer according to claim 8, wherein said engagement mechanism is composed of a protrusion radially projecting from a surface of said rod, and a flexible annular ring attached to the rear end of said cylinder and having a stopper portion on a movement path of said protrusion, and said engagement is released by deformation of the stopper portion of said annular ring by a pushing force in the axial direction of said rod.

10. The injector-type atomizer according to claim 8, wherein said engagement mechanism is composed of a protrusion radially projecting from a surface of said rod and an inner peripheral edge of the rear end of said cylinder, and said engagement is released when said protrusion is advanced to fit into said cylinder by a pushing force in the axial direction of said rod.

* * * * *